United States Patent [19]
Wagner et al.

[11] Patent Number: 5,626,227
[45] Date of Patent: May 6, 1997

[54] CASE FOR INSTRUMENT AND APPARATUSES FOR DENTISTRY

[75] Inventors: Thomas Wagner, Reiden; Roland Scacchi, Oberdorf; Pascal Rerat, Bubendorf; Paul Keller, Witterswil, all of Switzerland

[73] Assignee: Institut Straumann AG, Waldenburg, Switzerland

[21] Appl. No.: 442,933

[22] Filed: May 17, 1995

[30] Foreign Application Priority Data

Jun. 6, 1994 [CH] Switzerland ............... 1767194

[51] Int. Cl.⁶ ............................................. B65D 83/10
[52] U.S. Cl. .................. 206/369; 206/379; 206/762; 206/765; 211/69; 433/77; 433/79
[58] Field of Search ........................... 206/63.5, 369, 206/379, 759, 762, 765; 211/69; 433/77, 79; 422/300, 104

[56] References Cited

U.S. PATENT DOCUMENTS

| | | | |
|---|---|---|---|
| 1,684,417 | 9/1928 | Silberman | 206/369 |
| 3,583,556 | 6/1971 | Wagner | 206/373 |
| 4,050,894 | 9/1977 | Genis | 206/369 |
| 4,306,862 | 12/1981 | Knox . | |
| 4,503,972 | 3/1985 | Nelligan et al. | 206/379 |
| 5,108,287 | 4/1992 | Yee et al. | 433/77 |
| 5,172,810 | 12/1992 | Brewer | 206/369 |
| 5,368,161 | 11/1994 | Plais | 206/369 |
| 5,490,975 | 2/1996 | Dane | 422/300 |

FOREIGN PATENT DOCUMENTS

| | | |
|---|---|---|
| 2263915 | 12/1972 | Germany . |
| 3117264 | 4/1988 | Germany . |
| 3706569 | 9/1988 | Germany . |
| 624620 | 8/1978 | Russian Federation . |

*Primary Examiner*—David T. Fidei
*Attorney, Agent, or Firm*—Anderson Kill & Olick P.C.

[57] ABSTRACT

A case for dental instrument including a container, a lid for closing the container, a tray, and an insert arranged alongside of the container and including an instrument-receiving unit having a holder and a carrier and pivotable between a folded down position and an opened, vertical position, axle elements for supporting the instrument-receiving unit for pivotal movement, and elements for releasably holding the instrument-receiving unit in the opened position, with the carrier being provided with instrument-receiving insert openings and the holder being provided with stop arms for retaining the instruments in the insert openings.

9 Claims, 2 Drawing Sheets

CASE FOR INSTRUMENT AND APPARATUSES FOR DENTISTRY

BACKGROUND OF THE INVENTION

1. Field of the Invention

The invention relates to a case for storing medical instruments and apparatuses, for strong medical denistry, for example, dental burs, dental cutters, ratchets, screwdrivers, and devices such as endodontic aids.

2. Description of the Prior Art

With the prior art, dental instruments are stored in trays, either individually in bores, or together in larger bores. Dental apparatuses are also stored in special boxes.

The cases commonly used at present are of a design which is unfavorable from the application point of view. Thus, the stability and the clear arrangement of the instruments stored therein are for the most part very unsatisfactory. At the same time, it is often not possible to remove the instruments easily and safely using one hand. In addition, the risk of the cutting edges and bur points breaking upon contact with one another, with the case walls or with external objects is not generally prevented.

The dental material into which the instruments, such as burs and cutters, have to penetrate during working on the tooth is known to be hard and abrasive. Burs and milling cutters which are used on this material have to be very hard in order to guarantee an acceptable service life. These hard and wear-resistant bur and cutter materials are known to be brittle and friable. The cutting edges and points of such cutters and burs are therefore very susceptible to abrasion and breakage of the cutting edges, if they are carelessly handled, and they have to be stored safely without any wall contact whatsoever.

In addition to the abovementioned requirements, a case for medical instruments and apparatuses should also facilitate the repeatedly necessary cleaning and disinfection of the instruments and devices used in the field of dentistry. To this end, the case itself must not only be able to be cleaned thoroughly in a simple and hygienic manner, but must at the same time be capable of being used directly as a container for the instruments and devices which are to be sterilized in the steam bath, at a maximum of 135° C.

Cases for application in dentistry, which satisfy all the abovementioned requirements simultaneously, are not as yet known.

A transport container for spiral burs is disclosed in the PCT patent specification WO 92/15502, a variable number of spiral burs being held immobile in order to prevent any damaging contact of the bur points within the inner walls of the container. For this purpose the container has a bottom part which is joined by means of a hinge to a lid part, which is designed such that it can be swivelled downward to make contact with the bottom part. A plurality of rectangular receiving holders for spiral burs are secured on the bottom part. Receiver openings for spiral burs in each receiving holder are designed for receiving one or more spiral burs, each of which is equipped with a limit ring around it for the purpose of limiting the depth of insertion. A plurality of holding plates extend downward from the lid part. With the lid part closed, a separate holding plate is thus arranged between two adjacent receiver openings for spiral burs in such a way that the lower surface of the holding plate is arranged above the upper limit ring surfaces which are formed on the spiral burs introduced into the receiver openings. This ensures that each upward movement of the rings arranged on the spiral burs is limited. However, this design of the case has the disadvantage that with the lid part opened, a spiral bur can fall out from the receiver opening. In addition, each spiral bur has to be equipped with a limit ring, which is expensive.

A case for storing elongate instruments, such as spiral burs, thread-cutting taps and the like, is known from the patent specification DE 3500569 C1. The case has a lid part, and a bottom part attached to the latter, as well as a holder part, arranged on the bottom part, with guide holders for the instruments, which are aligned essentially perpendicular to the swivel axis of the bottom part. Each guide holder has two guide recesses, of which the first forms a central mounting, essentially free of play, for the instrument, and of which the second has a shape which permits a swivel movement of the instrument about the first guide recess in a plane perpendicular to the hinge axis of the bottom part. The disadvantage of this embodiment lies in the fact that the case has only a moderate stability, the instruments can fall out when the lid part is opened, and the movable parts and the guide holders cannot be reliably cleaned.

3. Objects of the Invention

For cases of the abovementioned type, the invention achieves the object of securing the instruments against any damage, be it during transportation, during opening or closing of the case, or in the event of hocks or movements during sterilization. The case according to the invention should in this respect not only offer a reliable solution preventing the instruments from inadvertently falling out, but should also reduce to a minimum any risk of injury to the user during removal or introduction of the instruments and apparatuses.

It should also be possible, for instance when making the case ready for introduction or removal of the instruments, for the case itself, and also for the parts of the case which have been opened up, to be positioned securely and be swivelled into a position facilitating removal. It would at the same time be expedient if the instruments which are to be stored were arranged in a line so that they could be seen clearly at all times. The individual parts of the case according to the invention should be of a straightforward and robust design. The novel case should be safe to handle and as easy as possible to clean. It should also be capable of being used directly for disinfection of the instruments and devices, which are stored therein, in the liquid and steam baths which it is desired to use in each case. Finally, it should be possible for the novel case to be used as a complete treatment unit with all instruments and apparatuses necessary for the dental treatment envisaged.

SUMMARY OF THE INVENTION

The above-discussed objects of the present invention are achieved by providing a case for dental instruments and apparatuses in which a container and an associated lid are provided with at least one tray, and at least one insert, extending alongside the tray, is arrange in the container, with the insert including a unit for receiving the instruments. The unit consists of a holder and a carrier. The unit can be folded about swivel axle elements into a folded down position parallel with the bottom of the case and into an opened, vertical position. The unit in the folded down position provides for play in the axle bearings and can be removed from the insert without auxiliary means. In the opened position the unit is immovably fixed in the axle glide, and is held releasably in this position by bulge means. The carrier has insert openings for receiving the instruments, with each insert opening having a shape which interacts with a stop arm on the holder in such a way that the instrument located in the insert opening is secured against positional displacement by the contact pressure of the respective stop arm. It is further provided a grip projecting above the instruments.

DETAILED DESCRIPTION OF THE PREFERRED EMBODIMENT

Figure 2:
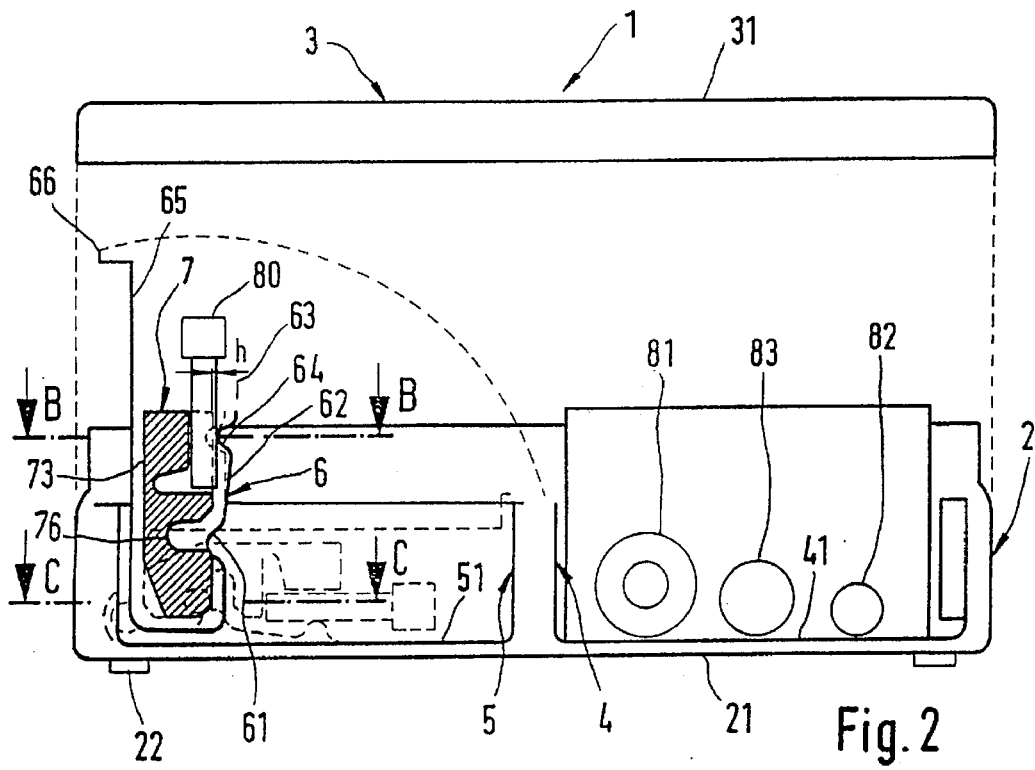
FIG. 2 shows a section through the case along the line A—A in FIG. 1, the holder and support being represented in a position in which they are opened up.
Figure 1:
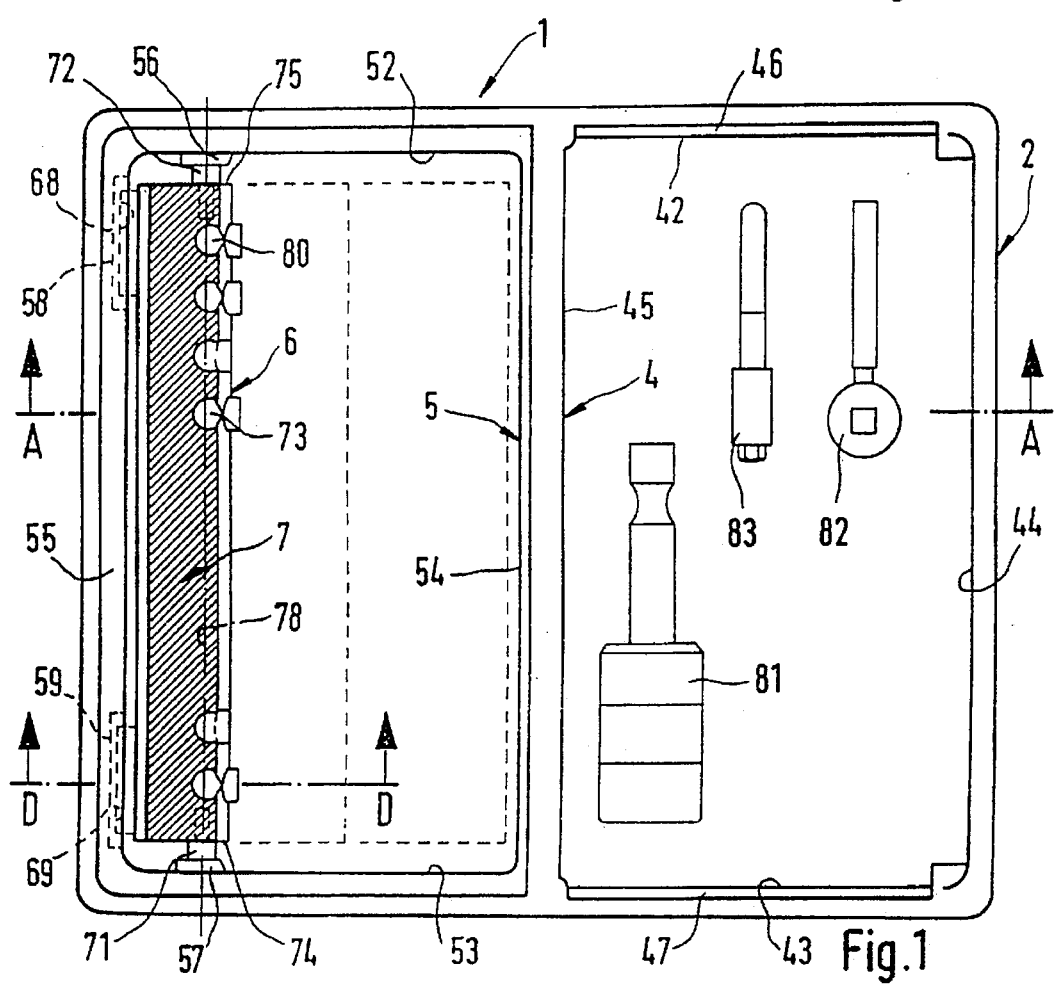
FIG. 1 shows an opened case for instruments and apparatuses in a plan view, with an insert arranged therein, together with holder and support, and also a tray.
Figure 3:
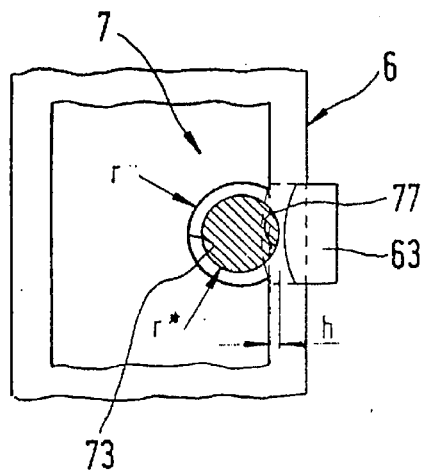
FIG. 3 shows a partial section along the line B—B in FIG. 2 through the mounting and the fixing means for an instrument, on an enlarged scale.
Figure 4:
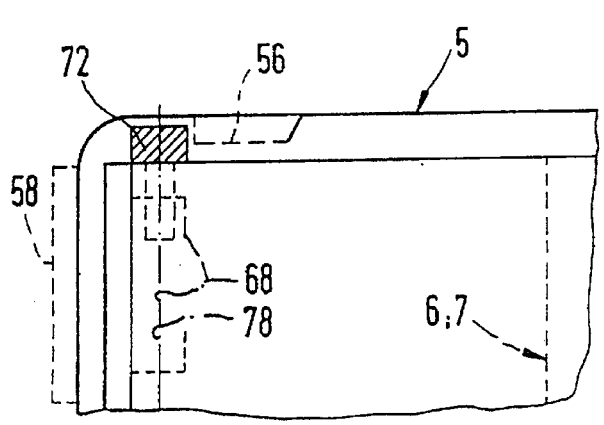
FIG. 4 shows a partial section along the line C—C in FIG. 2, with the unit in the closed position, on an enlarged scale.
Figure 5:
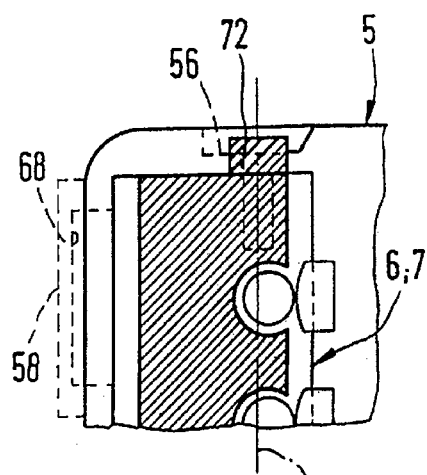
FIG. 5 shows a partial section along the line C—C in FIG. 2, with the unit in the opened position, on an enlarged scale.

The case 1 represented in FIGS. 1, 2 and 3 consists of a container 2, and of a lid 3 which can be placed on top. Both parts 2, 3 are preferably made of aluminum, which is surface-treated. The container 2 has a bottom 21 with hollows, and support feet 22. The lid 3 similarly has a cover 31 with hollows.

In the container 2 there is at least one tray 4 for receiving apparatuses 81–83, and at least one insert 5 for receiving instruments 80. Both parts 4 and 5 are made of stainless steel, for example.

The tray 4 has a bottom 41 with hollows. End walls 42, 43 with support strips 46, 47 issue from the narrow edges of said bottom 41, while side walls 44, 45 without support strips issue from its long edges. The end walls 42, 43 and side walls 44, 45 are designed widening upward, and the support strips 46, 47 are preferably bent inward.

The insert 5 has a bottom 51 with hollows. End walls 52, 53 issue from the narrow edges of said bottom 51, while side walls 54, 55 issue from its long edges. Here, the end walls 52, 53 each have a support strip, and one of the side walls 54, 55 has a third support strip, the three support strips being contiguous. Swivel journal guides 56, 57 are formed in the end walls 52, 53 for the purpose of receiving swivel journals 71, 72 of a carrier 7.

The carrier 7 is essentially rectangular in cross section. As a body, it has the shape of an elongate parallelepiped. The latter has, on its upper, narrow cover surface, insert openings 73 which are arranged in a straight line and are spaced apart uniformly from each other. These insert openings 73 extend from the upper cover surface of the carrier 7 almost to its bottom surface, maintaining a residual wall thickness. The insert openings 73 receive instruments 80 secure against tilting and with play. The carrier 7 moreover has a swivel axle 78, for which purpose it has, on its end walls 74, 75, the swivel journals 71, 72 which have already been mentioned. The carrier 7 can be folded down into a horizontal position parallel with the bottom, and can be opened up into a vertical position.

The carrier 7 is pushed into a holder 6 which is essentially U-shaped in cross section. A bead 61 in the one leg 62 of the holder 6 engages into a recess 76 of the carrier 7 and thus fixes, in conjunction with the other leg 65 of the holder 6, the position of the carrier 7 in the holder 6 in two of three directions. The one leg 62 of the holder 6 moreover lies opposite the insert openings 73 of the carrier 7.

Each insert opening 73 has an essentially cylindrical shape. It also has an open side surface 77 toward the one leg 62 of the holder 6. Taking this open side surface 77 of the insert openings 73 into account, the cross sectional areas of the insert openings 73 have the shape of a circle, from which one segment has been removed. The ratio of the curve height h of the removed circle segment to the circle radius r of the residual circle area preferably amounts here to ⅖, but can lie between ⅕ and ⅘ depending on the concrete example of application. The radius r* of the individual instrument shaft located in the insert opening 73 is in each instance slightly smaller than the circle radius r of the associated insert opening 73, but greater than the curve height h of the removed circle segment (written as a formula: h<r*<r), so that a part of the instrument shaft 80 protrudes outward through the open side surface 77 of the insert opening 73. The respective size of the circle radius r of the insert openings 73 in the carrier 7 must of course be adapted to the predetermined, standardized measurements of the individual instrument shaft.

Stop arms 63 are arranged on the one leg 62 of the holder 6 at a short distance from the front long wall of the carrier 7. Each insert opening 73 is assigned, at its open side surface 77, such a stop arm 63. Each stop arm 63 is in this instance designed with a bulge 64 in order, in conjunction with the insert opening 73, to hold the instruments 80 immobile by contact pressure, i.e. to secure them against moving in their insert openings 73. This securing of the instruments is guaranteed both when the unit 6, 7 is in the opened position and in the folded down position, and also when the unit 6, 7 is being removed from the insert 5. The stop arms 63 issue from, and are made of the same material as, the holder 6, i.e. the design is cost-effective and of simple technological concept.

Since the insert openings 73 are arranged in a line and in the longitudinal direction of the carrier 7, there is a clear view of the instruments 80 when the carrier 7 is in the opened position. That part of the instrument shaft in each instance protruding from the carrier 7 can be easily gripped with the pincers. The instrument 80 which is wanted can thus be removed from the carrier 7 easily, safely and in a perfectly hygienic manner.

The following statements are evident in conjunction with FIGS. 1, 4, 5, 6 and 7.

Figure 7:
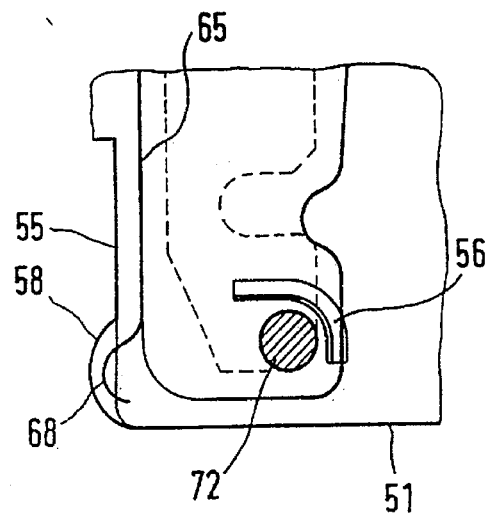
FIG. 7 shows a partial section along the line D—D in FIG. 1, with the unit in the opened position, on an enlarged scale.

The other leg 65 of the holder 6 has, at its free end, a rim 66 which is L-shaped in cross section. When the unit 6, 7 is folded down, the rim 66 can be used as a grip for opening the unit 6, 7, i.e. for moving it from its horizontal position in the container 5 into its vertical position by turning the whole unit 6, 7 through approximately 90° about the swivel axle 78 extending through the swivel journals 71, 72. The unit 6, 7 is in this instance held in bearings by means of the swivel journals 71, 72 interacting with the swivel journal guides 56, 57 of the insert 5, as shown in FIG. 7. A locking is obtained by virtue of the fact that two bulges 58, 59 in the rear side wall 55 of the insert 5 interact with two resilient beads 68, 69 at the lower corners of the leg 65 of the holder 6, since the resilient beads 68, 69 have to be bent back slightly under application of force when the unit 6, 7 is turned into the vertical position. In this way the unit 6, 7 locks in the opened position free of play, the movements of the swivel journals 71, 72 additionally being guided and limited by the one side wall 55 and the bottom 51 of the insert 5.

Figure 6:
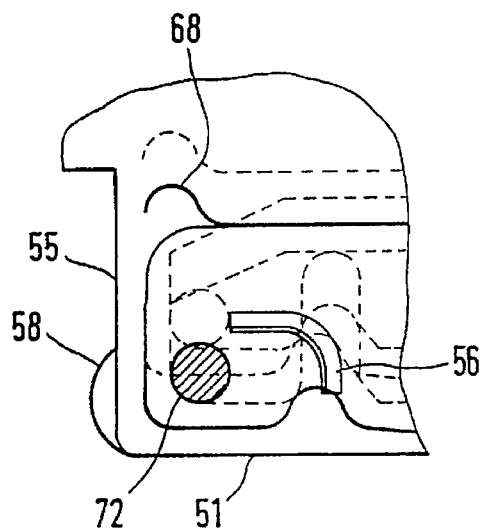
FIG. 6 shows a partial section along the line D—D in FIG. 1, with the unit in the closed position, on an enlarged scale.

In order to remove the unit consisting of holder 6 and carrier 7 from the insert 5, see FIG. 6, the unit 6, 7 is brought into the horizontal position. In this position, it can be lifted in the vertical direction and removed from the insert 5, the swivel journals 71, 72 fitting the gap between the swivel journal guide 56 or 57 and the one side wall 55.

The turning or folding of the unit 6, 7, consisting of holder 6 and carrier 7 in the insert 5, about the swivel axle 78 into the horizontal or vertical position, respectively, and the locking are made possible solely by the interaction of the resilient beads 68, 69 on the holder 6 and of the bulges 58, 59 on the insert 5 with the integrally formed swivel journals 71, 72 on the carrier 7 and the side wall 55 and bottom 51. No welding, soldering, screwing, riveting or other connections are used which have surfaces which are difficult to clean and sterilize. As will be readily appreciated by the specialist, the case can also be dismantled immediately into its individual parts in a few maneuvers. The fact that it can be dismantled into a small number of simple individual parts means that the case can be cleaned perfectly hygienically in a simple manner.

We claim:

1. A case for dental instruments and apparatus, comprising:

a container;

a lid for closing the container, at least one tray located in the container;

an insert located in the container alongside with the tray and including an instrument-receiving unit comprising a holder and a carrier, the instrument-receiving unit being pivotable between a folded down horizontal position in which the instrument-receiving unit can be removed from the insert, and an opened, vertical position;

swivel axles means for supporting the instrument-receiving unit for pivotal movement between the folded down and opened positions, the swivel axle means comprising swivel journals provided on opposite sides of the instrument-receiving unit and swivel journal guides arranged in opposite end walls of the insert for receiving the swivel journals; and means for releasably holding the instrument-receiving unit in the opened position, the holding means comprising resilient beads provided on the instrument-receiving unit and bulge means provided in a respective side wall of the insert for engaging the resilient beads, wherein the carrier has a plurality of insert openings for receiving dental instruments and the holder has a plurality of stop arms for immovably retaining the instruments in respective insert openings.

2. A case according to claim 1, wherein each insert opening has a cylindrical shape and has a cross-section of a circle with a cut-off segment, and wherein a ratio of a height of the cut-off segment to a radius of the circle is at least one-fifth and at most four-fifth.

3. A case according to claim 2, wherein the ratio of the height of the cut-off segment to the circle radius is two-fifth.

4. A case according to claim 1, wherein the holder and the stop arms are formed of a same material.

5. A case according to claim 1, wherein the insert openings extend parallel to each other and are spaced from each other by a same distance.

6. A case according to claim 1, wherein the holder has a leg having a free end, and an c-shaped rim provided at the leg free end, the rim forming a grip projecting above the instruments for enabling opening of the instrument-receiving unit.

7. A case according to claim 1, wherein the container, the lid, the tray, the insert, the holder, and the carrier are all formed of sterilizable materials and as separate elements forming a set of elements from which the case is assembled.

8. A case according to claim 1, wherein each insert opening has a shape enabling insertion of an instrument into the insert opening in a sliding manner.

9. A case according to claim 1, wherein the swivel journals provided on the instrument-receiving unit are coaxial.

* * * * *